(12) United States Patent
Enge (10) Patent No.: US 12,239,821 B2
(45) Date of Patent: *Mar. 4, 2025

(54) DEVICE FOR A MEDICAMENT CONTAINER

(71) Applicant: SHL Medical AG, Zug (CH)

(72) Inventor: Kasper Enge, Järfälla (SE)

(73) Assignee: SHL Medical AG, Zug (CH)

( * ) Notice: Subject to any disclaimer, the term of this patent is extended or adjusted under 35 U.S.C. 154(b) by 514 days.

This patent is subject to a terminal disclaimer.

(21) Appl. No.: 17/650,430

(22) Filed: Feb. 9, 2022

(65) Prior Publication Data

US 2022/0265932 A1 Aug. 25, 2022

Related U.S. Application Data

(63) Continuation of application No. 16/314,399, filed as application No. PCT/EP2017/064251 on Jun. 12, 2017, now Pat. No. 11,278,672.

(30) Foreign Application Priority Data

Jul. 6, 2016 (SE) .................................... 1650993-7

(51) Int. Cl.
*A61M 5/24* (2006.01)
(52) U.S. Cl.
CPC ....... *A61M 5/24* (2013.01); *A61M 2005/2407* (2013.01); *A61M 2005/2418* (2013.01)
(58) Field of Classification Search
CPC .......... A61M 5/178; A61M 2005/2403; A61M 2005/2433; A61M 2005/2437; A61M 2005/244; A61M 2005/2485; A61M 5/31; A61M 2005/2407; A61M 2005/2418; A61M 5/24
See application file for complete search history.

(56) References Cited

U.S. PATENT DOCUMENTS

2005/0277896 A1 12/2005 Messerli et al.
2009/0312715 A1* 12/2009 Monson ................ A61M 5/346
604/201

(Continued)

FOREIGN PATENT DOCUMENTS

| CN | 102917740 A | 2/2013 |
| TW | 201404418 | 2/2014 |
| WO | 2010/066589 A2 | 6/2010 |

*Primary Examiner* — Jason E Flick
(74) *Attorney, Agent, or Firm* — McDonnell Boehnen Hulbert & Berghoff LLP (57) ABSTRACT

A medicament container holder for securing a medicament container having a generally tubular body arranged with a proximally directed neck portion and a flange portion arranged with a pierceable septum. The medicament container holder has mechanical holding elements that interact with the flange portion for preventing movement of the medicament container in a distal direction and having mechanical fixation elements configured to interact with the flange portion for urging the flange portion in the distal direction against the holding elements, where the medicament container holder has attachment elements for a medicament delivery member. The mechanical fixation elements are configured to engage with the medicament delivery member when attached to the attachment elements, such as to exert a force in the distal direction on said flange portion.

18 Claims, 11 Drawing Sheets

(56) References Cited

U.S. PATENT DOCUMENTS

| | | |
|---|---|---|
| 2012/0143143 A1 | 6/2012 | Giambattista et al. |
| 2013/0046245 A1 | 2/2013 | Raab et al. |
| 2014/0142515 A1 | 5/2014 | Jugl et al. |
| 2014/0330213 A1 | 11/2014 | Hourmand et al. |
| 2016/0101235 A1 | 4/2016 | Holmqvist et al. |
| 2021/0196891 A1* | 7/2021 | Säll .................... A61M 5/2033 |

* cited by examiner

DEVICE FOR A MEDICAMENT CONTAINER

CROSS REFERENCE TO RELATED APPLICATIONS

The present application is a continuation of U.S. patent application Ser. No. 16/314,399 filed Dec. 29, 2018, which is a U.S. National Phase Application pursuant to 35 U.S.C. § 371 of International Application No. PCT/EP2017/064251 filed Jun. 12, 2017, which claims priority to Swedish Patent Application No. 1650993-7 filed Jul. 6, 2016. The entire disclosure contents of these applications are herewith incorporated by reference into the present application.

TECHNICAL AREA

The present disclosure relates to a device for a medicament container and in particular a medicament container holder to be used as a part of a medicament delivery device.

BACKGROUND

A vast majority of medicament delivery devices are arranged with some sort of medicament container that is holding the medicament to be delivered to a patient. Often the medicament container is placed releasably in the medicament delivery device, especially if the medicament delivery device is a so called re-usable device that is used many times and wherein an emptied medicament container is replaced with a new and full medicament container.

The medicament container is often held inside the medicament delivery device in order to avoid rattling of the medicament container but also in order to handle the forces that are exerted on the medicament container by e.g. an energized plunger rod during dose delivery. In many cases, the medicament container is placed in a dedicated medicament container holder inside the medicament delivery device. This may for example be the case if an automatic penetration is performed by the medicament delivery device. Then the medicament container holder is moved in the proximal direction by an appropriate force, whereby the medicament container with its medicament delivery member, for example an injection needle, also is moved in the proximal direction, causing a penetration of the injection needle.

Depending on the design of the medicament container, it is held in different ways. One common design is that the medicament container is arranged with a flange or collar at its distal end, especially syringe type medicament containers. Such medicament containers may then be supported at the flange. A risk is then that the force from a plunger rod on a stopper will break the flanges if the break-loose force on the stopper is high.

SUMMARY

The aim of the present disclosure is to remedy the drawbacks with the state of the art devices and in particular reducing the risk of breaking medicament containers when a force is applied on the stopper inside the medicament container.

This aim is solved by a medicament container holder provided with the features of the independent claim. Preferable solutions form the subject of the dependent patent claims.

According to one aspect of the disclosure, it comprises a medicament container holder for securing a medicament container, where the medicament container may comprise a generally tubular body arranged with a proximally directed neck portion, wherein the neck portion may be arranged with a pierceable septum.

For securing the medicament container, the medicament container holder may preferably comprise mechanical holding elements configured to interact with the neck portion for preventing movement of said medicament container in a distal direction. Further, the medicament container holder may comprise mechanical fixation elements configured to interact with the neck portion for urging said neck portion in the distal direction against the holding elements. The medicament container is thus held with its flange portion between the holding elements and the fixation elements, which will minimize any movement of the medicament container when the medicament container holder is placed in a medicament delivery device, whereby noise such as rattling is prevented or greatly reduced.

In order to safely secure medicament container, the medicament container holder may comprise attachment elements for a medicament delivery member, wherein the mechanical fixation elements are configured to engage with a medicament delivery member when attached to the attachment elements, such as to exert a force in the distal direction on the neck portion. With this solution the medicament container is fixedly held in place by the holding elements and the fixation elements and locked by the medicament delivery member. Thus the medicament delivery member has also a locking feature. A further advantage with this solution is that the distance between the medicament delivery member and the septum of the medicament container can be well defined by the dimensions of the fixation elements. Thereby any tolerance variations are minimized.

According to one aspect, the mechanical holding elements comprise a number of inwardly directed protrusions. These protrusions may be arranged with a wedge-shape such to facilitate the passing of the flange part of the medicament container when mounted in the medicament container holder. In this regard, the material of the medicament container holder may be flexible enough to allow an elastic flexing action in the radial direction when the medicament container passes. As an alternative, the material adjacent the holding elements may be weakened or removed in order to improve the elastic flexibility of the protrusions. For instance, slits may be arranged adjacent the protrusions.

In order to perform a fixating action, the fixation elements may be configured to be flexible movable in a generally longitudinal application and according to one feasible solution, the fixation elements may comprise generally radially directed arms, the free ends of which are configured to interact with the flange portion. In this regard, the free ends of the arms may be configured with protrusions which are configured to interact with flange portion.

As an alternative, the fixation elements may comprise a central ring-shaped member flexibly attached to the medicament container holder. With this solution, the fixation elements may comprise sections of material between the ring-shaped member and the medicament container holder, which sections are arranged flexible.

Further, the medicament container holder may be arranged as an integral part of a housing of a medicament delivery device or it may be arranged as a separate component of a medicament delivery device.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

DETAILED DESCRIPTION

Figure 1:
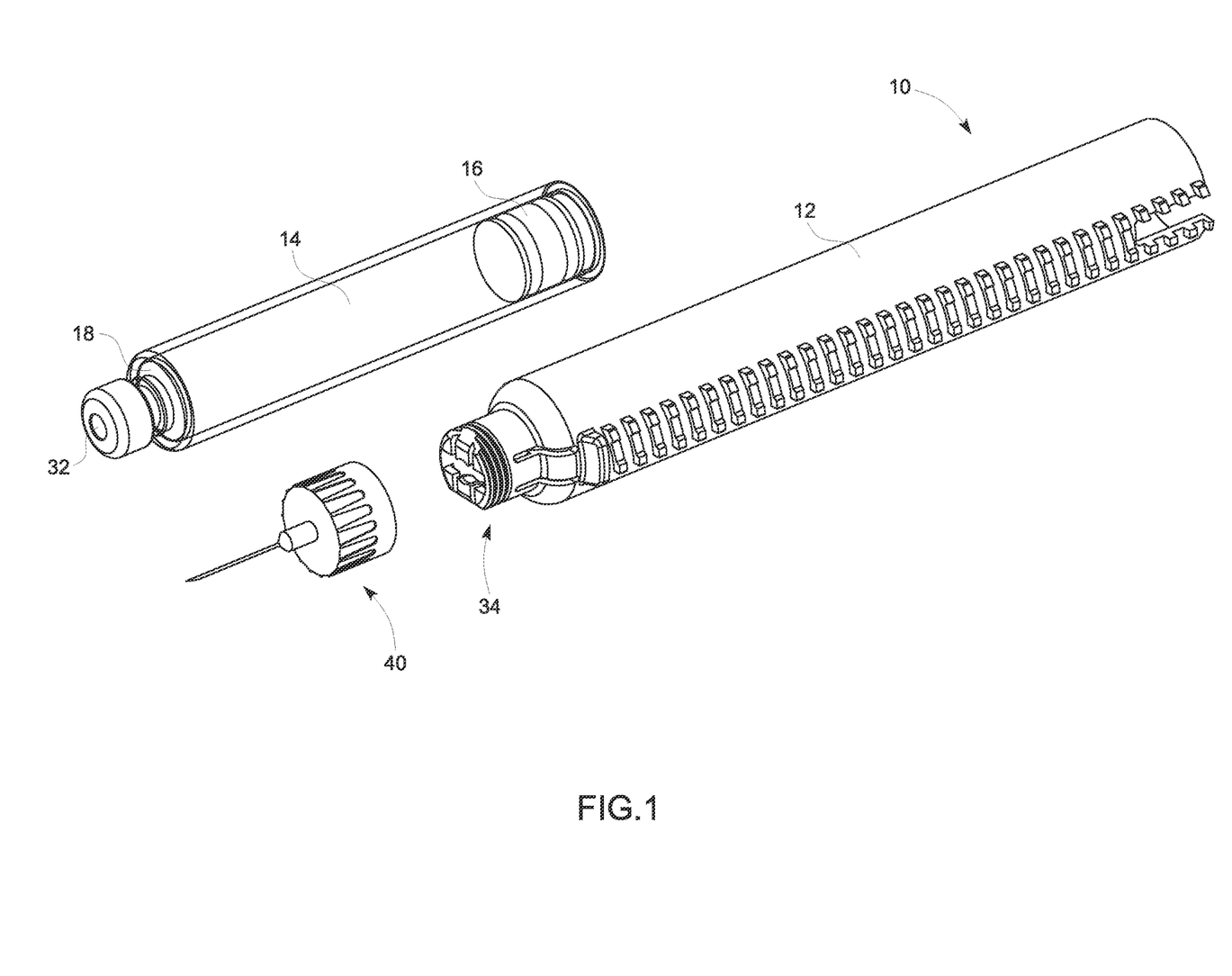
FIG. 1 is a perspective view of a medicament container holder and a medicament container.
Figure 2:
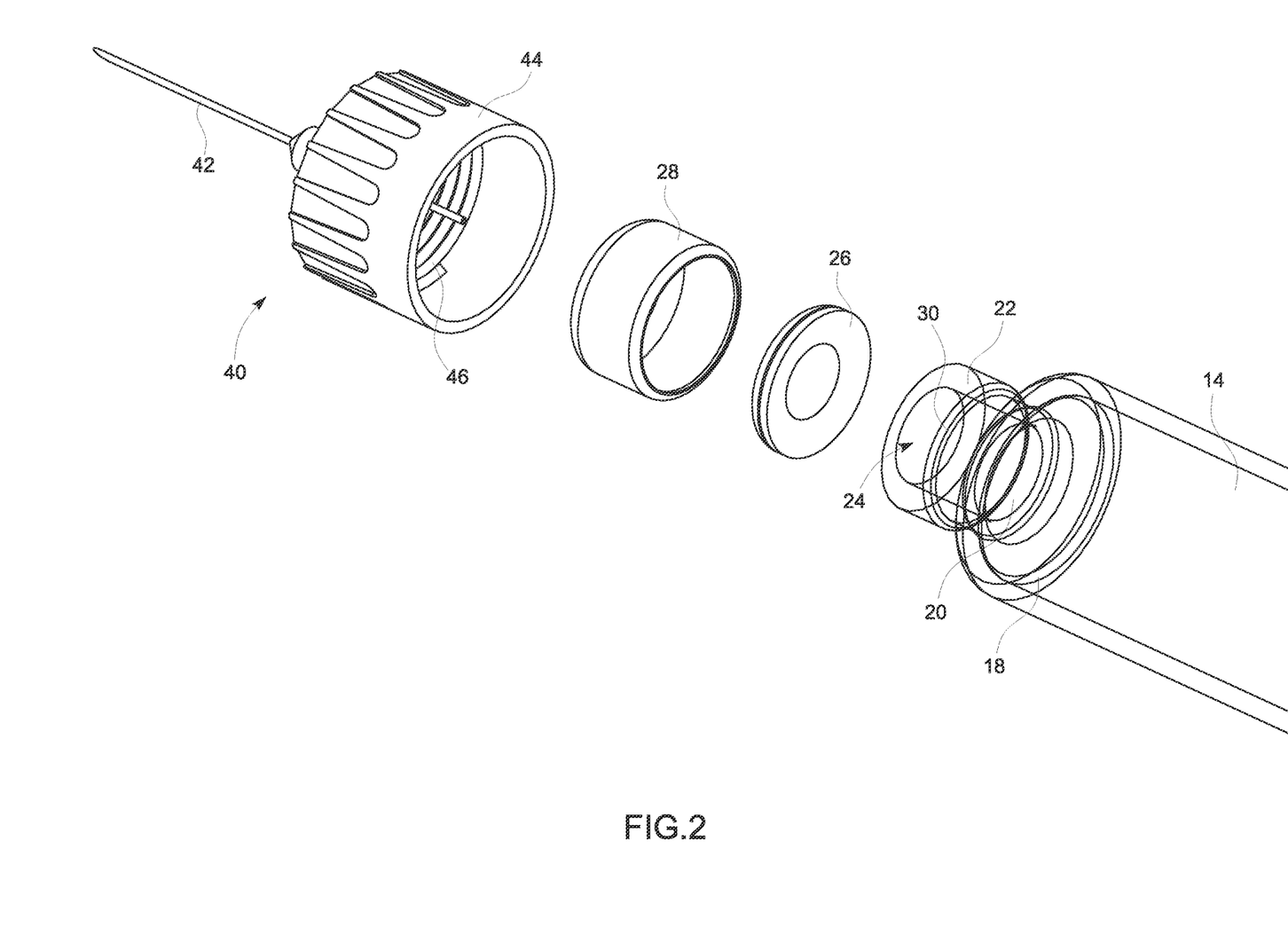
FIG. 2 is an exploded view of a neck portion of a medicament container and a medicament delivery member.

The first embodiment shown in the drawings 1 to 7 comprises a medicament container holder 10 having a generally tubular elongated body 12, FIG. 1. In this regard it is to be understood that the medicament container holder could be a part of a housing of a medicament delivery device as well or instead. The medicament container holder 10 is arranged to accommodate a generally tubular elongated medicament container 14. The medicament container 14 is arranged with a stopper 16 that is movable inside the medicament container 10 via e.g. a plunger rod acting from a distal direction. The proximal end of the medicament container 14 is provided with an annular shoulder 18 that transforms into a neck portion 20, FIG. 2. The neck portion 20 then transforms into a flange portion 22 surrounding a central passage 24. A septum 26 is positioned covering the central passage, which septum is made of a material that may be pierced by a sharp distal end of an injection needle, for instance a rubber membrane. The septum 26 is held in placed by a cap 28 surrounding the flange portion 22, wherein the distal edge of the cap is bent inwards at the distally directed surface 30 of the flange portion 22. The cap 28 has a central hole 32 through which the septum 26 is accessible.

Figure 3:
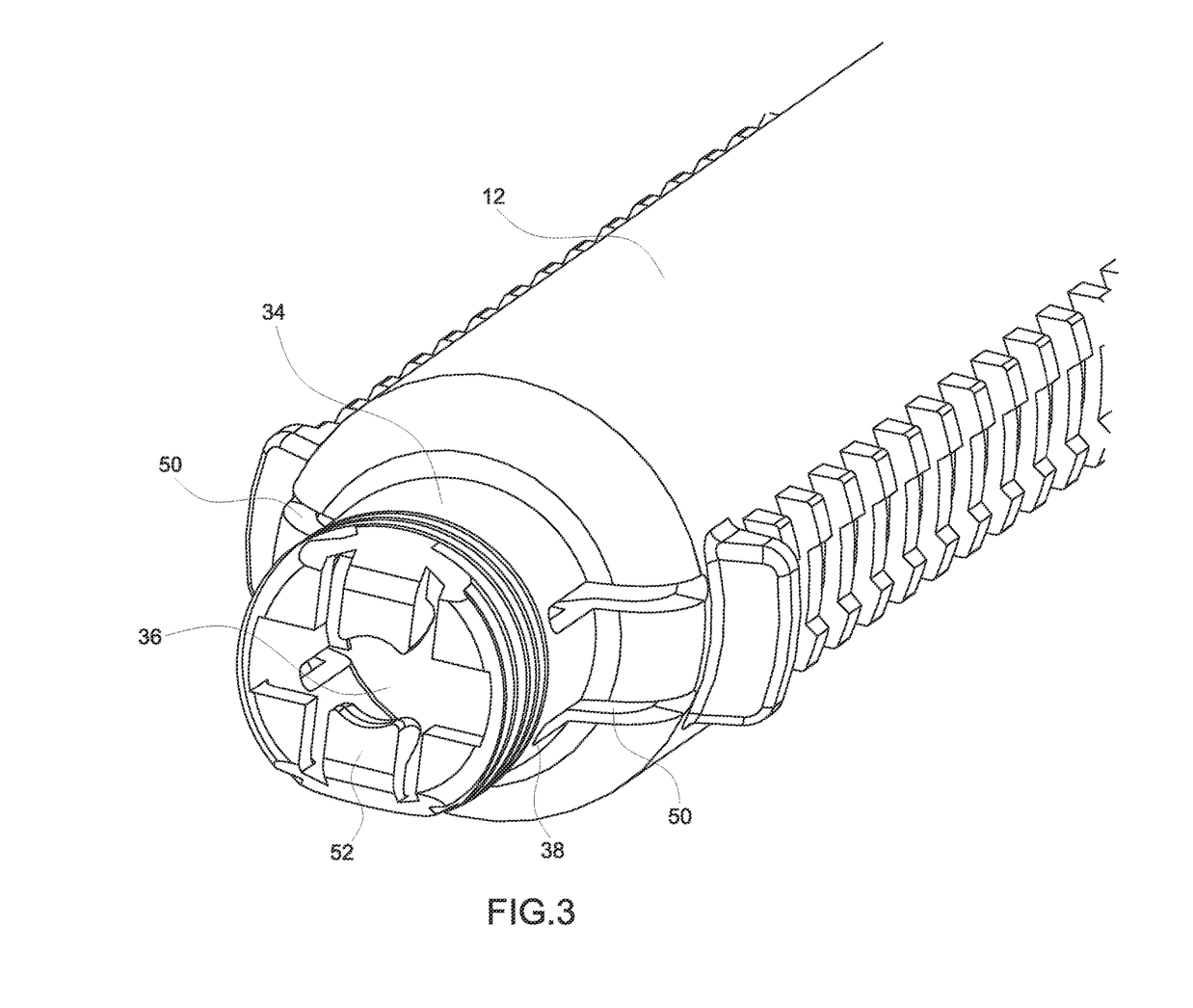
FIGS. 3-5 are detailed views of a proximal end of a first embodiment of a medicament container holder.
Figure 4:
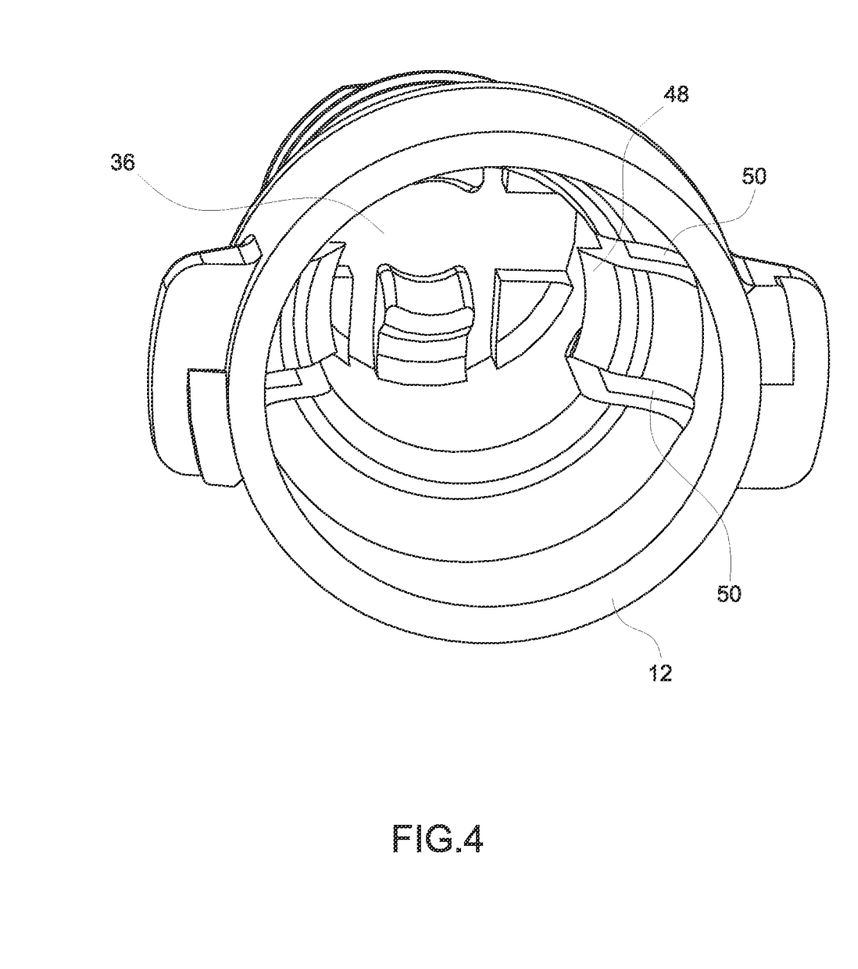
Figure 5:
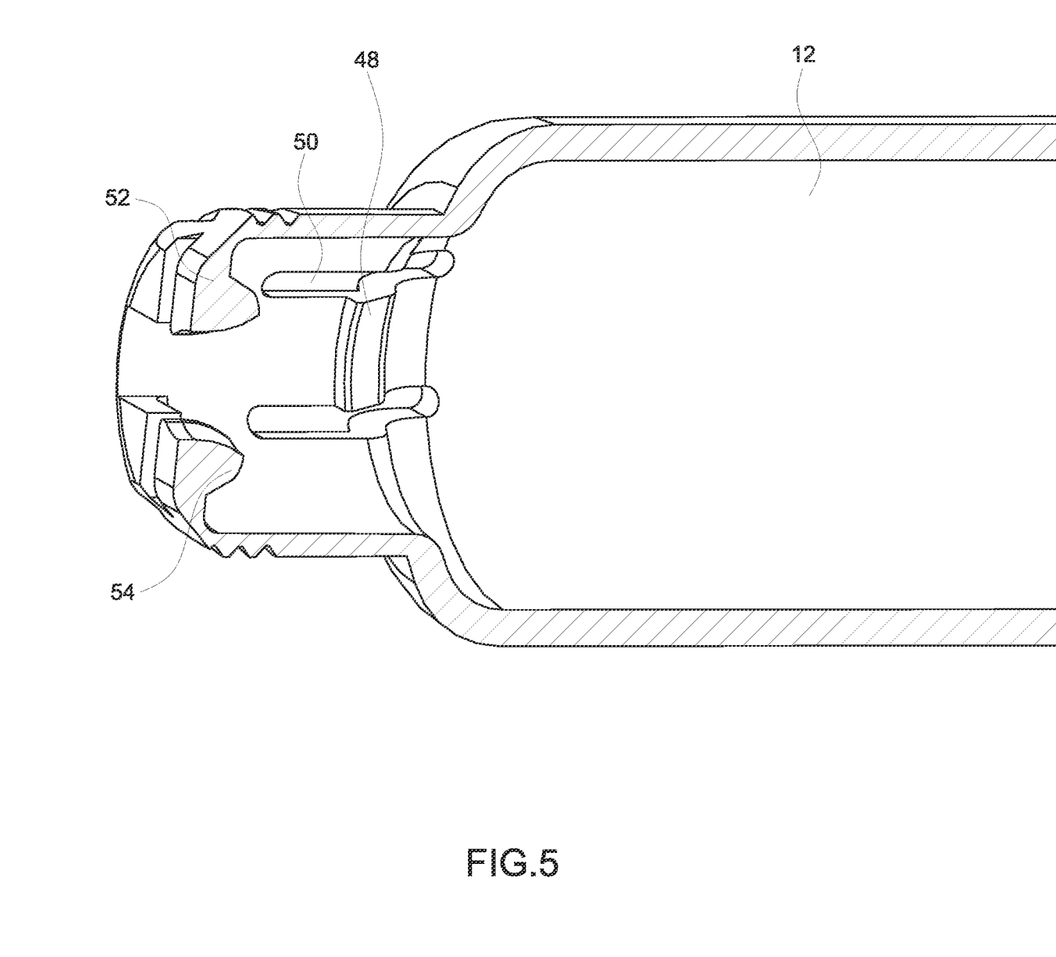
Figure 6:
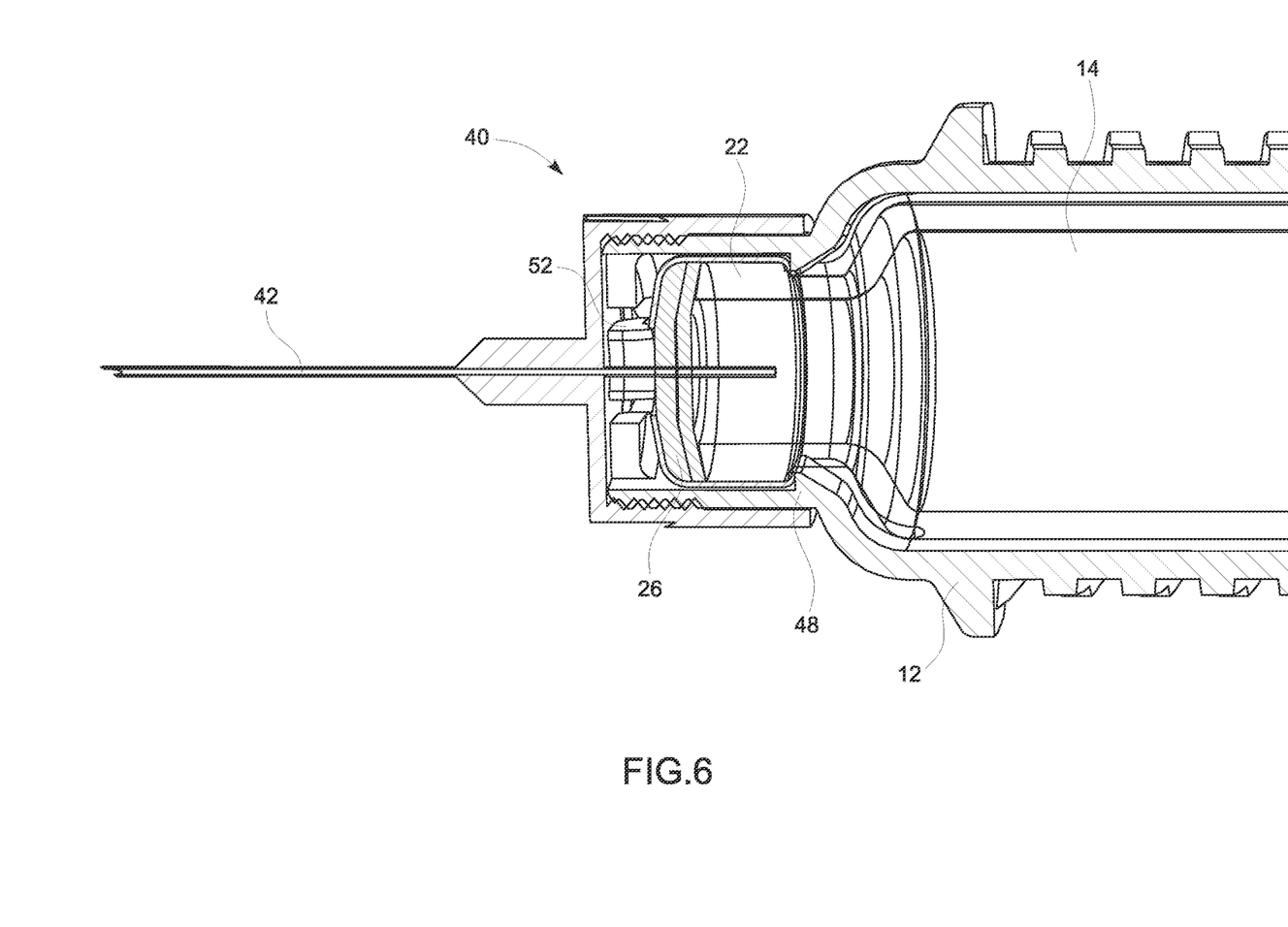
FIGS. 6-7 are cross-sectional views of a proximal end of the first embodiment with attached medicament delivery member.
Figure 7:
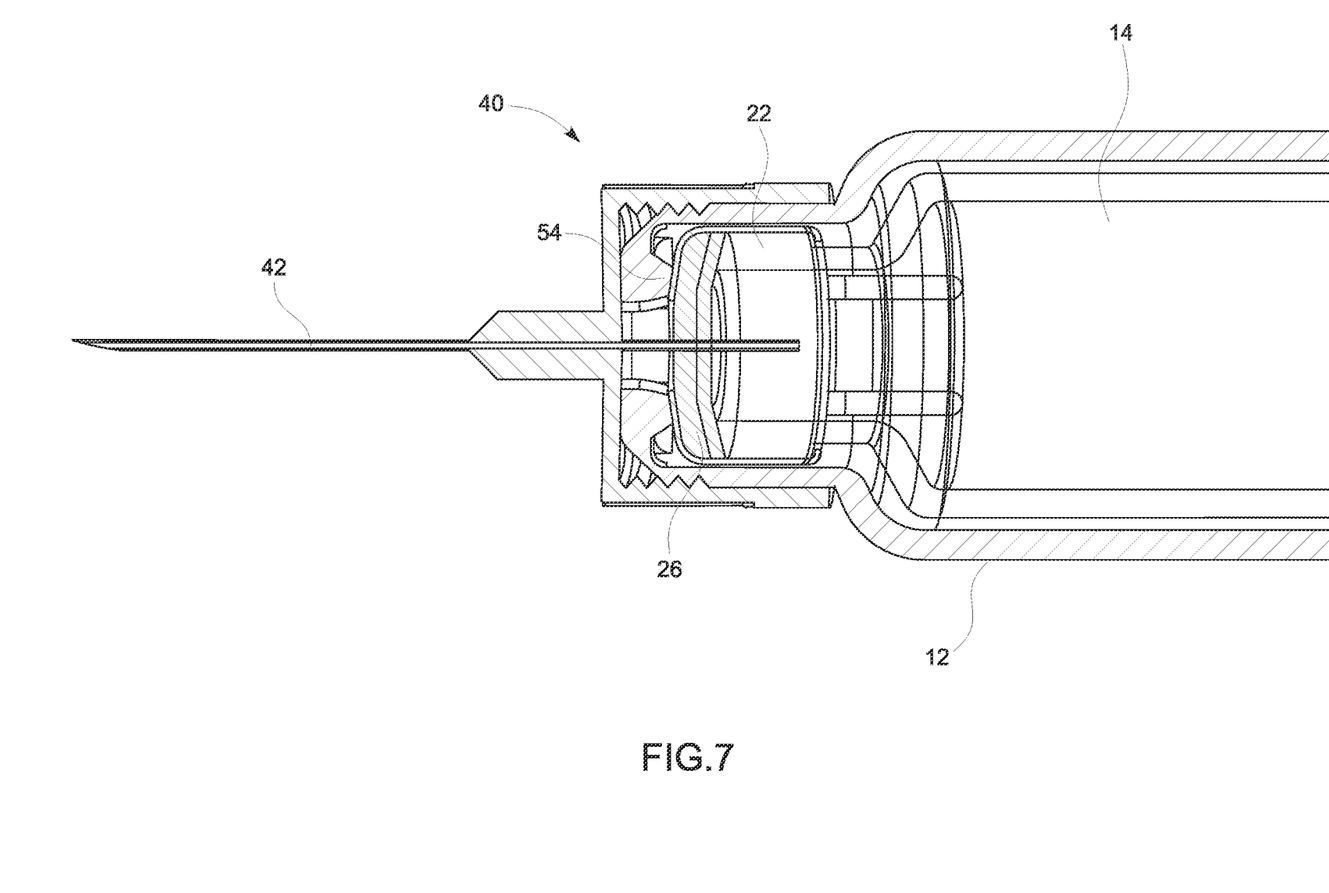

As mentioned, the medicament container 14 is intended to fit into the medicament container holder and for that purpose, the medicament container holder 10 is arranged with a neck portion 34 at its proximal end, having dimensions so as to accommodate the flange portion 22 with the cap 28 of the medicament container 14. The proximal end of the neck portion 34 of the medicament container holder 10 is provided with a passage 36 so as to get access to the interior of the medicament container holder 10 and thus the flange portion 22 of the medicament container 14 when placed in the medicament container holder 10. Further, the neck portion 34 of the medicament container holder is arranged with attachment elements 38 for a medicament delivery member 40. In the embodiment shown, the medicament delivery member is an injection needle 42 attached to a cap-shaped hub 44. It is however to be understood that other types of attachment elements may be utilized, such as bayonet connection, luer lock connections, snap-fit connections etc. The interior of the hub 44 is arranged with threads 46 that are to cooperate with external threads 38 on the neck portion 34 of the medicament container holder 10. According to the disclosure, holding elements are provided on the medicament container holder 10. In the embodiment shown in FIGS. 3 and 4, the holding elements comprise a number of wedge-shaped inwardly extending protrusions 48 that are formed on an inner surface of the neck portion of the medicament container holder 10. The protrusions 48 are wedge-shaped so as to allow the flange portion 22 of the medicament container 14 to pass the protrusions 48, whereby the material of the medicament container holder is such so as to allow elastic flexing in a radial direction. In order to improve the flexing capabilities, longitudinally extending slits 50 may be arranged on either side of the protrusions 48 as seen in FIG. 4.

The wedge-shaped protrusions 48 are positioned such that they will be placed abutting the distally directed surface 30 of the flange portion 22 of the medicament container 14 with proximally directed surfaces, which surfaces will act as reference surfaces as will be described. The medicament container holder is further arranged with fixation elements that are arranged to exert a certain force on the medicament container 14 in the distal direction, against the reference surfaces.

In the embodiment shown in FIGS. 1-7, the fixation elements comprise radially inwardly directed arms 52 having distally directed protrusions 54 at their free ends. Thus, when a medicament container 14 is placed in the medicament container holder 10 the proximal surface of the flange portion 22 will come in contact with the protrusions 54 of the arms 52 and the wedge-shaped protrusions 48 will pass the flange portion 22. The medicament container 14 is now held by the holding elements and the fixation elements, thereby preventing any rattling of the medicament container 14 inside the medicament container holder. When a medicament delivery member 40 now is attached to the neck portion of the medicament container holder a distally directed surface of the medicament delivery member will come in contact with proximally directed surfaces of the arms, FIGS. 6 and 7, thereby exerting a force on the medicament container 14 by the protrusions 54. Since the thickness of the protrusions 54 is well defined, the relationship between the septum 26 of the medicament container 14 and the medicament delivery member 42 is also well defined.

Figure 8:
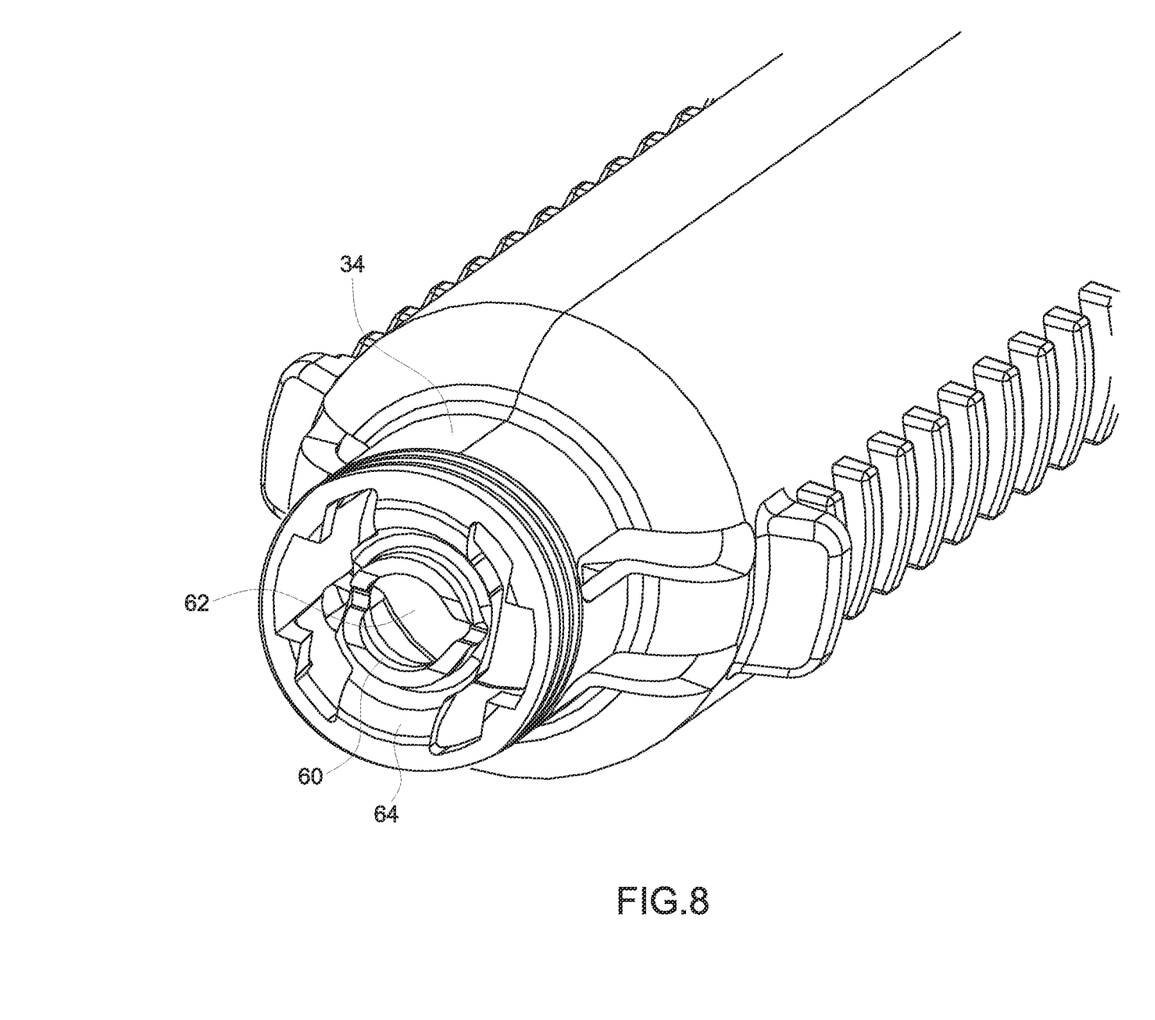
FIGS. 8-9 are detailed views of a proximal end of a second embodiment of a medicament container holder.
Figure 9:
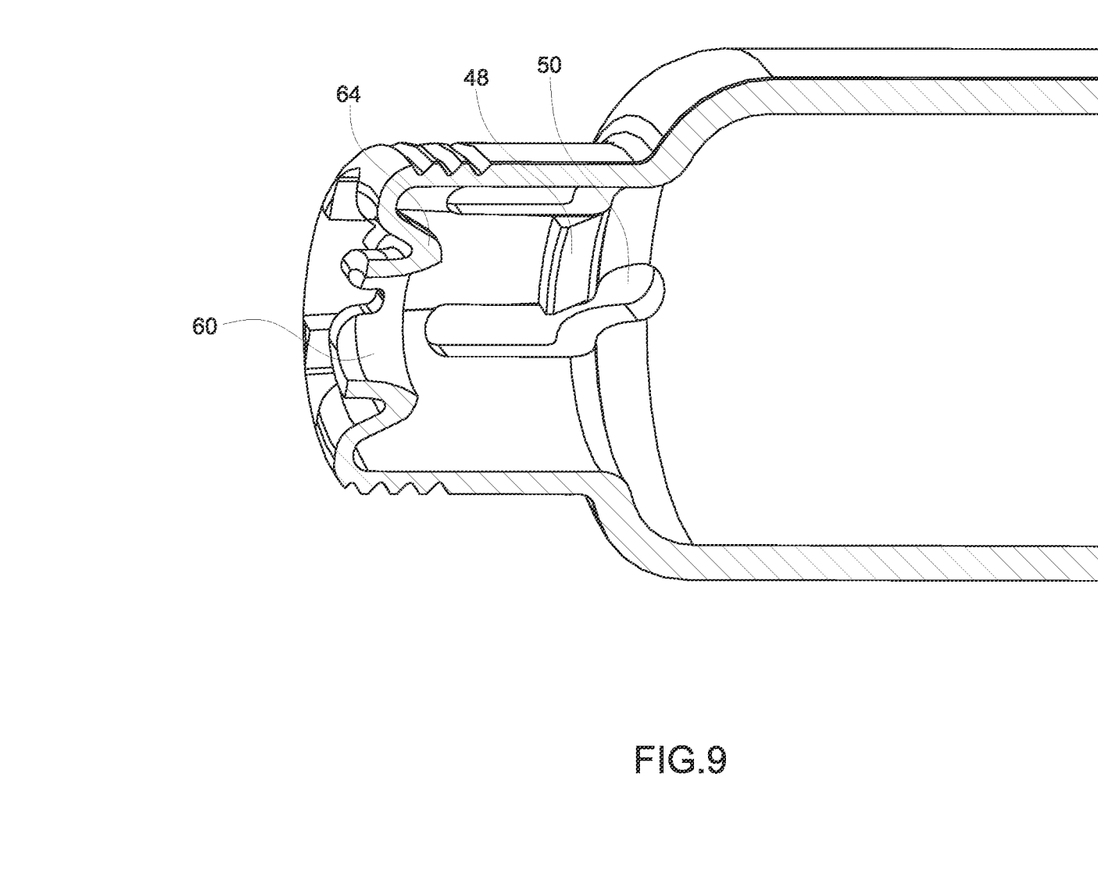
Figure 10:
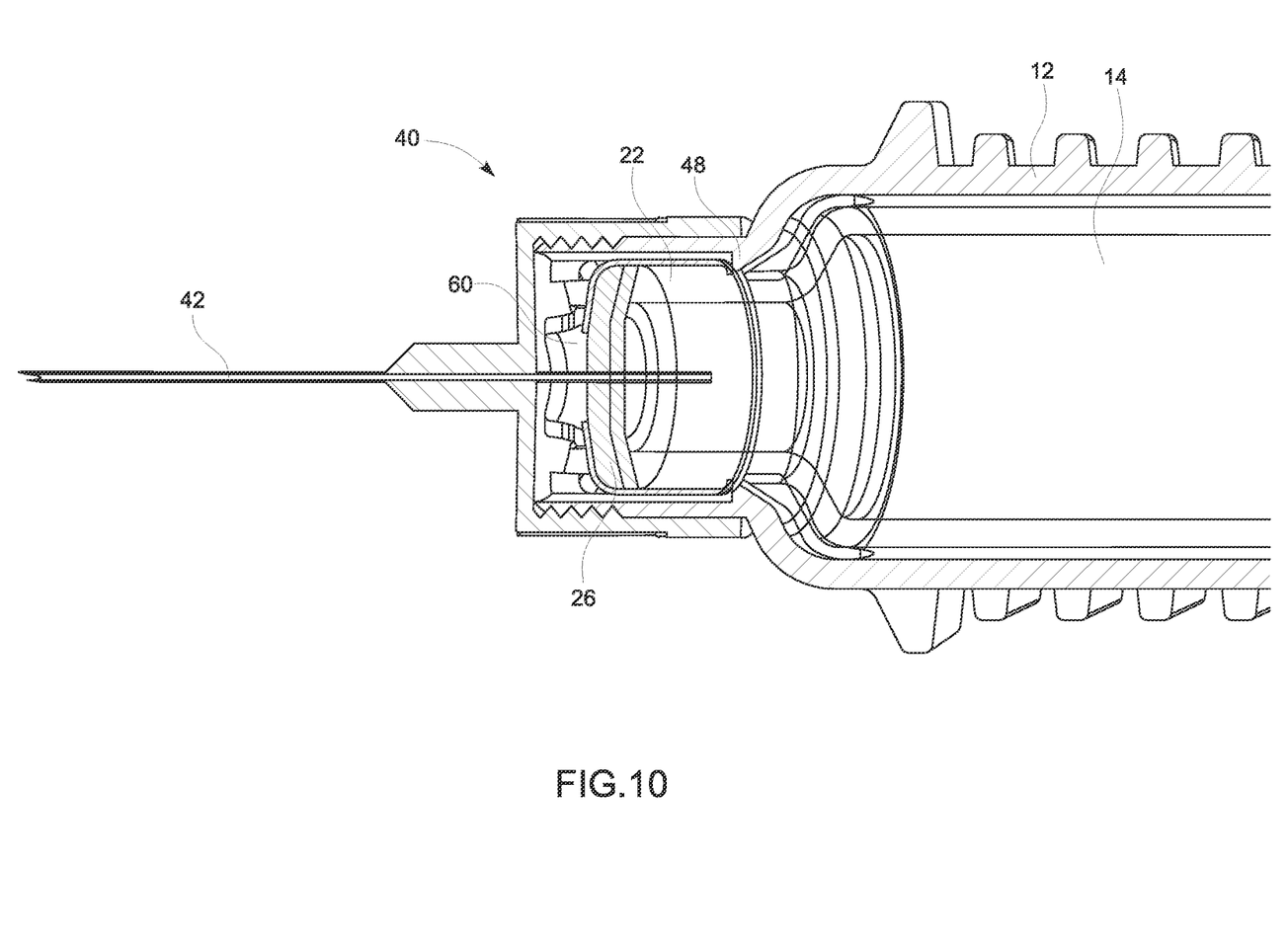
FIG. 10 is a cross-sectional view of a proximal end of the second embodiment with attached medicament delivery member.

FIGS. 8 to 10 show an alternative second embodiment of the present disclosure. The embodiment comprises a central ring-shaped fixation element 60 having a central passage 62, which fixation element 60 is held in position by bridging portions 64 provided on opposite sides of the fixation element and attached to the neck portion 34, FIG. 8. The land portions 64 have a curved shape as seen in FIG. 9 and will provide a flexing action in the longitudinal direction. As with the previous embodiment, when a medicament container 14 is placed in the medicament container holder 10, the proximally directed surface of the flange portion 22 will come in contact with distally directed surfaces of the fixation element 60. The wedge-shaped protrusions 48 will also pass the flange portion 22 of the medicament container, FIG. 10, and will abut the distally directed surface of the flange, creating a holing function in the distal direction of the medicament container 14.

Figure 11:
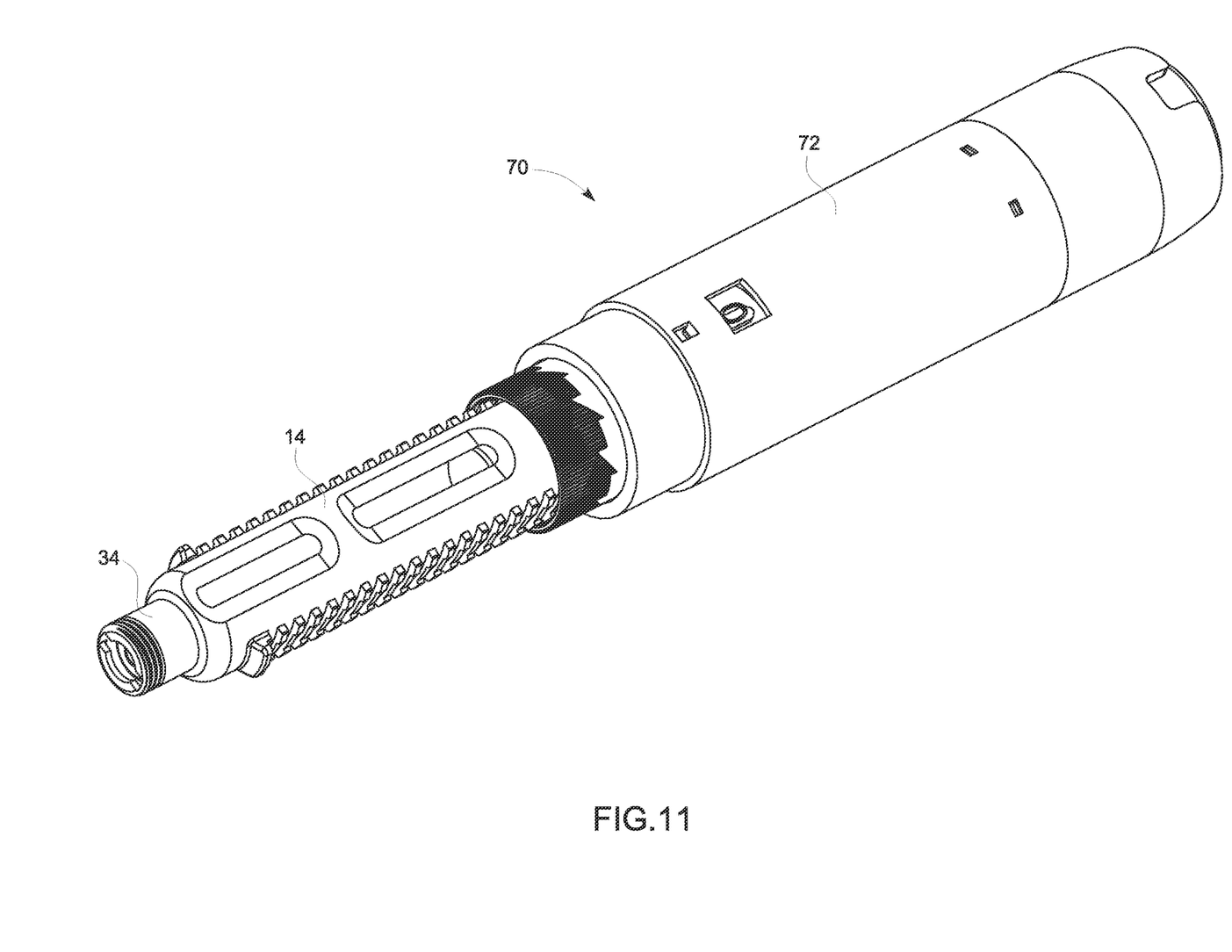
FIG. 11 is a perspective view of a medicament delivery device comprising a medicament container holder according to the disclosure.

FIG. 11 shows a medicament delivery device 70 in which a medicament container holder 10 according to the disclosure may be arranged. In this regard, as seen in the figure, the medicament container holder 10 is an integral part of the housing 72 of the medicament delivery device 70. It is however to be understood that the medicament container holder could as well be a separate component of the medicament delivery device.

I claim:

1. A medicament container holder, comprising:
a neck portion positioned at a proximal end of the medicament container holder;
a plurality of inwardly directed protrusions formed on an inner surface of the neck portion;
at least two radially inwardly directed arms having distally directed protrusions at their free ends, wherein the at least two radially inwardly directed arms are separate from and are not directly coupled to the plurality of inwardly directed protrusions, and wherein the at least two radially inwardly directed arms are configured to flex in a longitudinal direction; and
attachment elements for attaching a medicament delivery member to the medicament container holder.

2. The medicament container holder according to claim 1, wherein the at least two radially inwardly directed arms are configured to engage with the medicament delivery member when the medicament delivery member is attached by said attachment elements to the medicament container holder, such as to exert a force in an axial distal direction on a flange portion of a medicament container.

3. The medicament container holder according to claim 1, wherein the plurality of inwardly directed protrusions are configured to flex in a radial direction.

4. The medicament container holder according to claim 3, further comprising:
a plurality of cut-outs arranged adjacent the plurality of inwardly directed protrusions for providing flex in the radial direction.

5. The medicament container holder according to claim 1, wherein the at least two radially inwardly directed arms further comprise a central ring-shaped member flexibly attached to the medicament container holder.

6. The medicament container holder according to claim 5, wherein the at least two radially inwardly directed arms further comprise sections of material between the ring-shaped member and the medicament container holder, and wherein the sections of material are flexible.

7. The medicament container holder according to claim 1, wherein the medicament container holder is arranged as an integral part of a housing of a medicament delivery device.

8. The medicament container holder according to claim 1, wherein the medicament container holder is arranged as a separate component of a medicament delivery device.

9. The medicament container holder according to claim 1, wherein the attachment elements comprise an external threaded surface on the neck portion of the medicament container holder.

10. The medicament container holder according to claim 1, wherein the plurality of inwardly directed protrusions are wedge-shaped.

11. A medicament delivery device, comprising:
a medicament container comprising a generally tubular body arranged with a proximally directed neck portion and a flange portion arranged with a pierceable septum; and
a medicament container holder having a generally tubular elongated body which is arranged to accommodate the medicament container, the medicament container holder comprising:
a neck portion positioned at a proximal end of the medicament container holder;
a plurality of inwardly directed protrusions formed on an inner surface of the neck portion;
at least two radially inwardly directed arms having distally directed protrusions at their free ends, wherein the at least two radially inwardly directed arms are separate from and are not directly coupled to the plurality of inwardly directed protrusions, and wherein the at least two radially inwardly directed arms are configured to flex in a longitudinal direction; and
an attachment element that is configured to engage with a medicament delivery member when the medicament delivery member is attached by the attachment element to the medicament container holder, such as to exert a force in an axial distal direction on the flange portion of the medicament container.

12. The medicament delivery device of claim 11, wherein the medicament delivery device is a re-usable medicament delivery device where the medicament container can be removed from the medicament container holder.

13. The medicament delivery device according to claim 11, wherein the at least two radially inwardly directed arms are configured to flex in a radial direction when the flange portion is moved axially relative to the medicament container holder.

14. The medicament delivery device according to claim 11, further comprising one or more cut-outs arranged adjacent the plurality of inwardly directed protrusions for providing flex in a radial direction.

15. The medicament delivery device according to claim 11, wherein the at least two radially inwardly directed arms urge the flange portion in the axial distal direction against the plurality of inwardly directed protrusions.

16. The medicament delivery device according to claim 11, wherein the at least two radially inwardly directed arms further comprise a central ring-shaped member flexibly attached to the medicament container holder.

17. The medicament delivery device according to claim 16, wherein the at least two radially inwardly directed arms further comprise sections of material between the ring-shaped member and the medicament container holder, and wherein the sections of material are flexible.

18. The medicament delivery device according to claim 11, wherein the plurality of inwardly directed protrusions are wedge-shaped.

* * * * *